United States Patent
Thompson et al.

(10) Patent No.: US 10,281,368 B2
(45) Date of Patent: *May 7, 2019

(54) NATURAL GAS LIQUID PRESSURE REGULATING VAPORIZER SAMPLING SYSTEM

(71) Applicant: Mustang Sampling, LLC, Ravenswood, WV (US)

(72) Inventors: Kenneth O. Thompson, Ravenswood, WV (US); Micah A. Curtis, Ravenswood, WV (US)

(73) Assignee: Mustang Sampling, LLC, Ravenswood, WV (US)

( * ) Notice: Subject to any disclaimer, the term of this patent is extended or adjusted under 35 U.S.C. 154(b) by 81 days.

This patent is subject to a terminal disclaimer.

(21) Appl. No.: 15/116,862

(22) PCT Filed: Feb. 11, 2015

(86) PCT No.: PCT/US2015/015423
§ 371 (c)(1),
(2) Date: Aug. 5, 2016

(87) PCT Pub. No.: WO2015/123302
PCT Pub. Date: Aug. 20, 2015

(65) Prior Publication Data
US 2017/0167954 A1    Jun. 15, 2017

Related U.S. Application Data

(60) Provisional application No. 61/938,905, filed on Feb. 12, 2014.

(51) Int. Cl.
*G01N 1/10* (2006.01)
*G01N 1/44* (2006.01)
(Continued)

(52) U.S. Cl.
CPC ............... *G01N 1/10* (2013.01); *G01N 1/14* (2013.01); *G01N 1/20* (2013.01); *G01N 1/22* (2013.01);
(Continued)

(58) Field of Classification Search
None
See application file for complete search history.

(56) References Cited

U.S. PATENT DOCUMENTS 3,053,077 A    9/1962    Tracht
3,421,336 A    1/1969    Lichtenberger
(Continued)

FOREIGN PATENT DOCUMENTS

CN    103370568 B    5/2015
WO    2012/145606 A2    10/2012

OTHER PUBLICATIONS

International Application No. PCT/US2015/015423, Notification of Transmittal of the International Search Report and the Written Opinion of the International Searching Authority, or the Declaration, dated Jun. 25, 2015.
(Continued)

*Primary Examiner* — Benjamin R Whatley
(74) *Attorney, Agent, or Firm* — Cahn & Samuels, LLP (57) ABSTRACT

Provided herein is a system and method for natural gas liquid sample conditioning including an insulated cabinet having a sample input, a vaporizer, a heated regulator, a gas sample outlet, and a control system for preventing phase separation and or re-liquification of the conditioned sample before entry into an associated analyzer and in a specific embodiment, featuring an automatic shutdown system to prevent sample liquid from further processing and passage to an associated analyzer.

22 Claims, 4 Drawing Sheets

(51) Int. Cl.
  *G01N 1/22* (2006.01)
  *G01N 1/14* (2006.01)
  *G01N 1/20* (2006.01)
  *G01N 33/22* (2006.01)

(52) U.S. Cl.
  CPC ......... *G01N 1/2247* (2013.01); *G01N 1/2294* (2013.01); *G01N 1/44* (2013.01); *G01N 33/225* (2013.01); *G01N 2001/2238* (2013.01); *G01N 2001/2261* (2013.01)

(56) References Cited

U.S. PATENT DOCUMENTS

| | | | |
|---|---|---|---|
| 3,720,092 | A | 3/1973 | Reinecke |
| 4,007,626 | A | 2/1977 | Roof et al. |
| 4,735,259 | A * | 4/1988 | Vincent .................. G01N 30/30 165/135 |
| 5,205,177 | A * | 4/1993 | DuBrock, Jr. ....... G01N 1/2258 73/863.12 |
| 6,044,825 | A | 4/2000 | Carter et al. |
| 7,162,933 | B2 | 1/2007 | Thompson et al. |
| 7,484,404 | B2 | 2/2009 | Thompson et al. |
| 8,056,399 | B2 | 11/2011 | Thompson et al. |
| 8,307,843 | B2 | 11/2012 | Patterson et al. |
| 8,966,969 | B2 | 3/2015 | Kriel et al. |
| 9,057,668 | B2 | 6/2015 | Thompson et al. |
| 9,164,016 | B2 | 10/2015 | Barere |
| 9,285,299 | B2 | 3/2016 | Thompson |
| 2006/0000298 | A1 * | 1/2006 | Thompson ........... G01N 1/2214 73/863.81 |
| 2006/0201235 | A1 † | 9/2006 | Thompson |
| 2009/0151427 | A1 * | 6/2009 | Thompson ................ F17C 6/00 73/23.41 |
| 2009/0193884 | A1 | 8/2009 | Moore et al. |
| 2010/0012201 | A1 * | 1/2010 | Welker ................. F16K 15/028 137/535 |
| 2012/0011919 | A1 * | 1/2012 | Kriel ...................... G01N 30/88 73/23.35 |
| 2012/0048881 | A1 | 3/2012 | Drube |
| 2012/0272715 | A1 | 11/2012 | Kriel et al. |
| 2013/0263680 | A1 * | 10/2013 | Barere ..................... F17C 7/04 73/863.12 |

OTHER PUBLICATIONS

"White Paper on Liquid Hydrocarbon Drop Out in Natural Gas Infrastructure," NGC+ Liquid Hydrocarbon Dropout Task Group, Feb. 28, 2005.
Technical White Paper "Sample Liquid Petroleum Gas (and other high vapor pressure gas/liquids)",Sentry Equipment Corp, Tec 1.621 Rev. 0.
Intellectual Property Office of Singapore, Search Report, Application No. 11201606436S, dated Jul. 10, 2017.
European Patent Office, Application No. 15748549, Extended Search Report, dated Sep. 8, 2017.
Brad Massey, Williams, "Basics for New Engineering/Project Managers", Natural Gas Sampling Technology Conference, pp. 28-33, Jan. 22-23, 2014. New Orleans.
A+ Corporation, LLC, "2012 Product Catalog", pp. 1-90, Aug. 21, 2012.†
A+ Corporation, LLC, "ACES", pp. 1-4, May 16, 2013.†
A+ Corporation, LLC, "Genie Heated Regulator Model GHR", 2 Pages, Sep. 15, 2006.†
Mustang Sampling, LLC,"MIV2 Mustang Intelligent Vaporizer Sampling System", Product Bulletin for MIV series Vaporizer Sampling System (2 pages) Dec. 19, 2010, https://web.archive.org/web/20101219135937/http://www.mustangsampling.com:80/product/Ing/.†
Natural Gas Sampling Technology Conference, "NGS Tech 2007", Proceedings of Natural Gas Sampling Technology Conference, 143 Pages, Jan. 15, 2007.†
A+ Corporation, LLC, "Genie Vaporizer", Product Bulletin for Model GV of Genie Vaporizers, 2 pages, Sep. 18, 20016.†

* cited by examiner
† cited by third party

NATURAL GAS LIQUID PRESSURE REGULATING VAPORIZER SAMPLING SYSTEM

PRIORITY CLAIM

This application is a 371 national stage application from international application PCT/US 2015/015423 filed on Feb. 11, 2015 and claims priority to U.S. provisional patent application Ser. No. 61/938,905 filed Feb. 12, 2014.

TECHNICAL FIELD

This invention relates to and improvement allowing for collecting and conditioning samples containing heavier hydrocarbons from liquid natural gas inputs and, more particularly, to thermal conditioning of pipeline samples from a natural gas liquid source such as shale to maintain gas at a low pressure without re-liquification for analysis.

BACKGROUND

Gaseous NGL (natural gas liquid) not being cryogenic, after vaporization tends to include considerable entrained liquid natural gas. The presence of such entrained liquids undermines the qualitative accuracy of the energy value of the measured gas. This problem has been exacerbated with the substantial development of NGL recovery from fracking.

Unlike a typical gas obtained from conventional sources, NGL introduces a new analytical complication due to the presence of heavy hydrocarbons (e.g. those composed of more than five carbon atoms and generally in liquid form) not present in streams obtained from traditional gas wells. For example, widegrades containing a substantial range of methane through C5 and heavier components, e.g., asphalts, a material with vaporization temperatures in the 300-400° F. (148-204° C.) range, may cool sufficiently to cause phase separation and resulting component non-uniformity depending on when the measurement is taken depending on where in the phase transition curve. It is the stratification of lighters and heavier constituents that creates such deviations and skews the analysis. Reliquification following vaporization before analysis creates an even more serious scenario. Because the large majority of GCs do not operate properly at temperatures below 150° F. (65° C.) and above 180° F. (82° C.) and pressures under 10 psig, if a liquid is introduced into a conventional gas chromatograph (GC), it floods and disables the analyzer.

Many processing facilities for NGL rely on multiple and redundant, up to twenty-five gas chromatograph, and moisture analyzers, most being disposed midstream. It is well known that such analyzers, particularly gas chromatographs, are expensive—costing up to $50,000 each. In the event of flooding of a GC, it must be shut down and rebuilt or even replaced. In addition to the costs of processing interruptions occasioned by such shut downs, substantial maintenance, labor and equipment costs also result.

Many sample takeoff and conditioning units incorporate a liquid block feature to avoid the flooding problem. It has been found, however, that disposing of such a conventional liquid block, removes temperature and pressure limitations within the conditioning cabinet to thereby permit complete vaporization of the significantly increased "liquid heavies".

SUMMARY OF INVENTION

It is an object of the present invention to provide a novel, liquid natural gas sampling system and method that provides an alternative to and provides improved performance over the prior art in the context of NGL containing liquid heavies.

Another object of an aspect of the present invention is to provide protection against flooding of an associated gas analyzer from liquid intrusion.

Another object of the invention is to reduce the cost of equipment and labor associated with in-line, real-time analysis of heavy hydrocarbon and liquid containing NGL.

Yet another object of the invention is to provide a system permitting NGL sampling and analysis that prevents development of two/multiphase separation of vapor and or liquid.

Still a further object of the invention is to monitor the parameters of a conditioning system and interrupt sample analysis processing upon detection of pre-established parameter deviation thresholds and/or power loss.

These and other objects are satisfied by a system for extracting and conditioning for analysis by a gas sample analyzer of a non-cryogenic natural gas liquid sample composition containing a substantial range of methane through C5 and heavier components including asphalts, the system comprising:

a) an insulated cabinet;
b) a non-cryogenic liquid sample input line;
c) a vaporizer mounted in said insulated cabinet for flash vaporizing the non-cryogenic liquid connected to the input line;
d) a vaporized sample output line;
e) a heated pressure regulator mounted in said insulated cabinet connected directly to the vaporized sample output line for receiving a vaporized sample;
f) an output sample gas conduit line to communicate the vaporized sample to a gas sample analyzer located outside the insulated cabinet, said output conduit line connected at one end to the heated pressure regulator;
g) a controller electrically connected to the vaporizer and the heated pressure regulator, said controller being connected to an electrical power source, the controller for monitoring the temperature and pressure of the vaporized sample outputted from the heated pressure regulator to fall within an acceptable operation range of the gas sample and analyzer.

The system of the invention characterized in a second embodiment comprising a speed loop associated with the vaporizer.

The system of the invention characterized in a third embodiment further comprising a vent line for pressure relief in the event that the gas sample outputted from the heated regulator is above the acceptable operational range of the gas sample analyzer.

The system of the invention characterized in a fourth embodiment comprising a communications facility associated with the controller.

The system of the invention characterized in a fifth embodiment further characterized by a solenoid actuated valve disposed in the sample input line.

The system of the invention characterized in a sixth embodiment further characterized by a solenoid actuated valve disposed between the liquid filter and the input of the vaporizer for interrupting flow of the liquid sample to the vaporizer.

The system of the invention characterized in a further embodiment comprising a system for extracting and conditioning a non-cryogenic liquid sample for analysis by a downstream analyzer, the system characterized by:

a) an insulated cabinet;
b) a non-cryogenic liquid sample input line;

c) a vaporizer mounted in said insulated cabinet for flash vaporizing the non-cryogenic liquid to a flash-vaporized sample, said vaporizer being connected to the input line;

d) a vaporized sample output line connected to said vaporizer;

e) a heated pressure regulator mounted in said insulated cabinet and to said vaporized gas sample output line, for receiving the flash-vaporized gas sample from the vaporized sample output line;

f) an output conduit line to a gas sample analyzer located outside the insulated cabinet, said output gas conduit line connected at one end to the heated pressure regulator; and g) a controller for monitoring processing conditions in the insulated cabinet including activating a solenoid valve to interrupt liquid flow into the vaporizer upon detection of processing conditions deviating from pre-set ranges, the controller being in operation signal communication with the vaporizer, the heated pressure regulator, solenoid valve, and pressure transmitters, for monitoring sample pressure as the sample passes through the system to the vaporized sample output line to be within acceptable operation ranges, the controller being connected to an electrical power source, and a communications facility for remotely communicating monitored conditions.

The system of the invention characterized in a still further embodiment of the immediately previous embodiment further characterized by a filter and associated speed loop disposed in the sample input line.

The system of the invention characterized in a second still further embodiment further characterized by the solenoid valve being electrically connected to the controller and having a normally closed position which upon activation releases pressurized air to actuate a valve disposed in the non-cryogenic liquid sample input line to shut off sample flow.

The system of the invention characterized in a third still further embodiment further characterized by the a plurality of solenoid valves being electrically connected to the controller, each of the solenoid valves having a normally closed position which upon activation each releases pressurized air to actuate an associated valve disposed in the non-cryogenic liquid sample input line to shut off liquid flow to the vaporizer and in the vaporized sample output line to shut off vapor sample flow to the gas sample analyzer.

The system of the invention characterized in a fourth still further embodiment further characterized by a thermocouple input associated with the pas sample analyzer in communication with the controller to actuate the solenoid valves to shut off sample flow when the detected temperature of the pas sample analyzer falls below a predetermined minimum.

In this detailed description, references to "one embodiment", "an embodiment", or "in embodiments" mean that the feature being referred to is included in at least one embodiment of the invention. Moreover, separate references to "one embodiment", "an embodiment", or "embodiments" do not necessarily refer to the same embodiment; however, neither are such embodiments mutually exclusive, unless so stated, and except as will be readily apparent to those skilled in the art. Thus, the invention can include any variety of combinations and/or integrations of the embodiments described herein.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the root terms "include" and/or "have", when used in this specification, specify the presence of stated features, steps, operations, elements, and/or components, but do not preclude the presence or addition of at least one other feature, step, operation, element, component, and/or groups thereof.

As used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus.

For definitional purposes and as used herein "connected" includes physical, whether direct or indirect, affixed or adjustably mounted, as for example, the communication unit is connected to the a PID controller either directly or through a conventional wireless linkage when spaced apart. Thus, unless specified, "connected" is intended to embrace any operationally functional connection.

As used herein, and unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

As used herein "substantially," "generally," and other words of degree are relative modifiers intended to indicate permissible variation from the characteristic so modified. It is not intended to be limited to the absolute value or characteristic which it modifies but rather possessing more of the physical or functional characteristic than its opposite, and preferably, approaching or approximating such a physical or functional characteristic.

In the following description, reference is made to the accompanying drawings which are provided for illustration purposes as representative of a specific exemplary embodiment in which the invention may be practiced. The following illustrated embodiment is described in sufficient detail to enable those skilled in the art to practice the invention. It is to be understood that other embodiments may be utilized and that structural changes based on presently known structural and/or functional equivalents may be made without departing from the scope of the invention.

DETAILED DESCRIPTION

Figure 1:
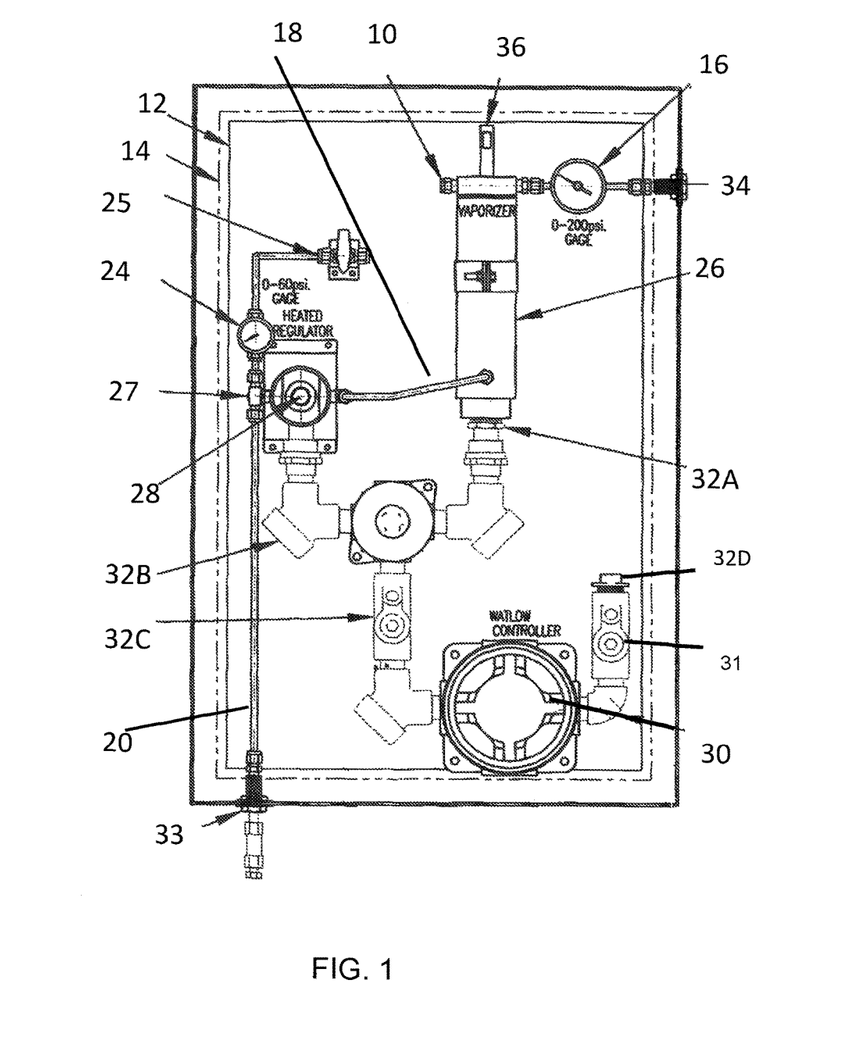
FIG. 1 is a schematic illustration of an embodiment of the natural gas liquid pressure regulating vaporizer system according to the invention.

FIG. 1 illustrates an embodiment of an inventive, single stream, natural gas liquid sample vaporizer system 10 . The system comprises a cabinet 12 preferably conforming in standards to a Class 1, Division 1 Group C, D, t3 (<200.degree. C.) requirements. The cabinet 12 is insulated fully with insulation 14 to maintain an internal elevated temperature.

The internal cabinet components include gas lines and 20, in line pressure gauges 16 and 24, a sample NGL vaporizer 26 such as a 375 watt Mustang Vaporizer available from Mustang Sampling of Ravenswood, W. Va. US, and a 200 watt heated pressure regulator 28 both being securely mounted within the insulated cabinet 12.

Affixed to an appropriately dimensioned feedthrough in the exterior cabinet wall and projecting therefrom is an encased PID controller system 30 such as Watlow Single Controller (EZ-Zone) available from Watlow of St. Louis, Mo., US which is electrically interconnected and controls the sample system components. The controller 30 is electrically connected to an appropriate power source and incorporates a digital communication connection either providing standard hardwire connections, e.g., RS 485 or USB, or wireless communication technology.

The PID controller 30 is electrically connected to internal cabinet components through hard wiring passing through sealed feedthrough conduits 32A, 32B, 32C, and 32D comprising appropriately-diametered, galvanized conduit (e.g., ¾ inch) with associated seal fittings reducers and the like. The construction of the feedthroughs and associated conduits must meet applicable standards such as NEC Sec. 500 (2011).

Turning to the gas sample pathway in respect to the cabinet 12 contemplated by the illustrated embodiment, the gas sample typically travels from a NGL extraction point through a small, sample gas line, generally consisting of small diameter stainless steel tubing connecting to a feedthrough 34 formed in a wall of the cabinet 12. Upon entry into the cabinet interior, the heavy hydrocarbon containing sample travels through the line to heated liquid sample vaporizer 26. The vaporizer 26 maintains the sample liquid below its bubble point pressure and temperature until it enters a low volume flash chamber having a very large heat transfer surface area where the sample is instantaneously vaporized. Heat for vaporization is transferred from an electrical cartridge heater associated with the vaporizer and connected to the controller 30. The flash chamber serves to maintain a homogeneous sample vapor that is representative of the actual liquid sample composition.

The junction of the vaporizer input may incorporate a pressure remediating speed loop or vent 36 to prevent sample over pressurization during the vaporizing step. That speed loop/vent which may incorporate an intermediate one-way check valve, is connected to the cabinet exterior via feedthrough vent. Such a speed loop and its function are described in Assignee's earlier issued U.S. Pat. No. 7,484,404, the content of which is incorporated in its entirety herein by reference. The particular form, diaphragm or piston, of the regulator is selectable by a user for a particular installation. Notably, diaphragm regulators are believed to provide superior performance in the case of liquid sample streams.

The vaporized sample is output through line 18 to the heated pressure regulator 28 where it is subject to both pressure and temperature conditioning and exits the heated regulator through a T connector 27 that feeds the vaporized sample to sample output line 20 and internal vent line 25 for venting vaporized samples exceeding an analyzer-safe pressure as measured by the gauge 24. and the properly heated and, pressurized vapor sample is communicated to an associated analyzer through the sample output 33 disposed in an appropriately isolated feedthrough feeding through the cabinet exterior that may include a venting capability featuring bug/insect resistant vent.

In ordinary operation, the vaporized liquid sample passes from the vaporizer to the heated regulator at high temperature and pressure to prevent dew point drop out/Joule-Thomson condensation of heavy hydrocarbons in the vaporized sample stream by maintaining heating the sample during the pressure reduction, the sample stream has been properly conditioned for passage out of the cabinet via sample analyzer feedthrough. The system itself preferably incorporates a communications facility to permit remote monitoring and control system allowing for changes to the system when deemed appropriate.

Figure 2:
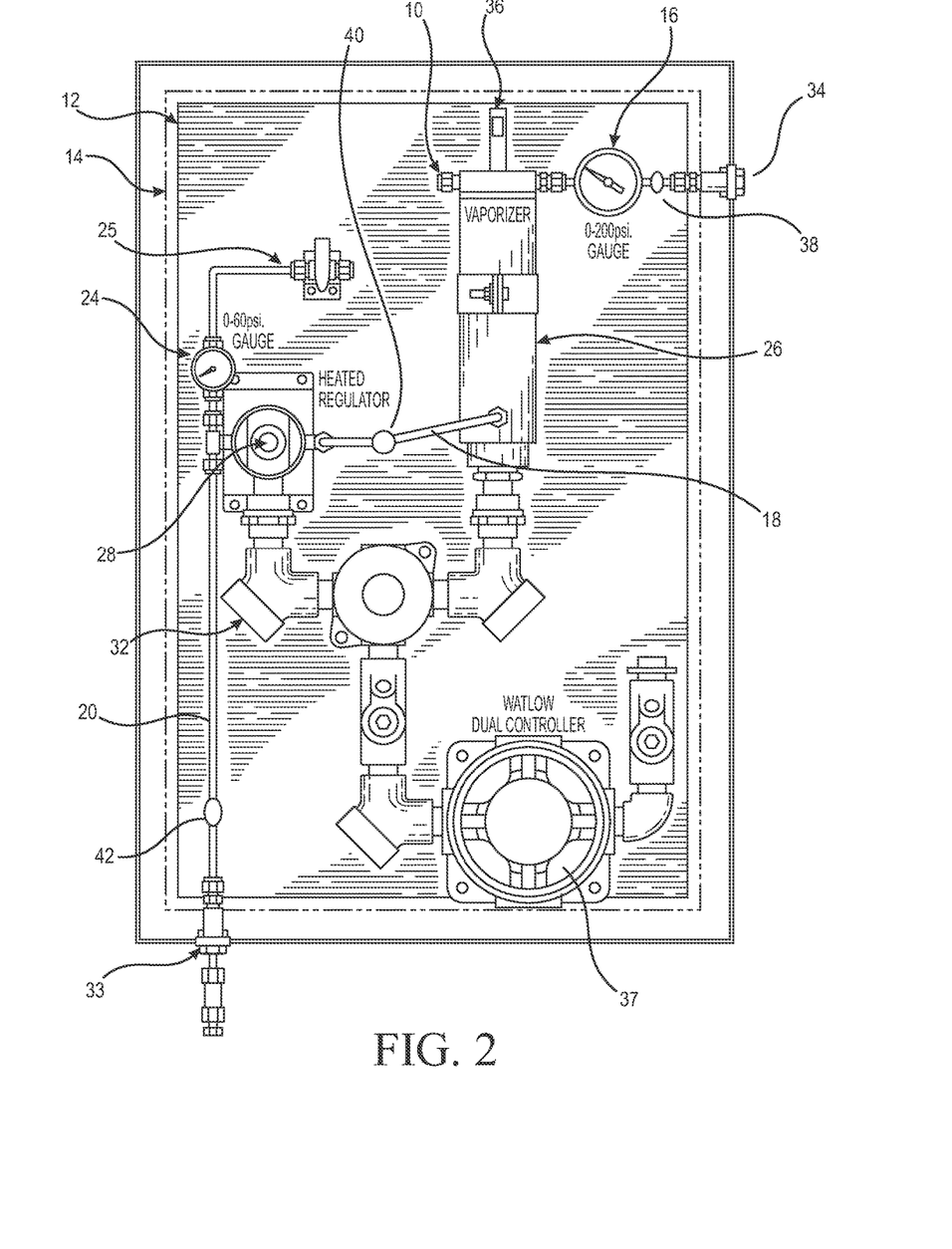
FIG. 2 is schematic illustration of an alternative embodiment of the natural gas liquid pressure regulating vaporizer system according to the invention.
Figure 3:
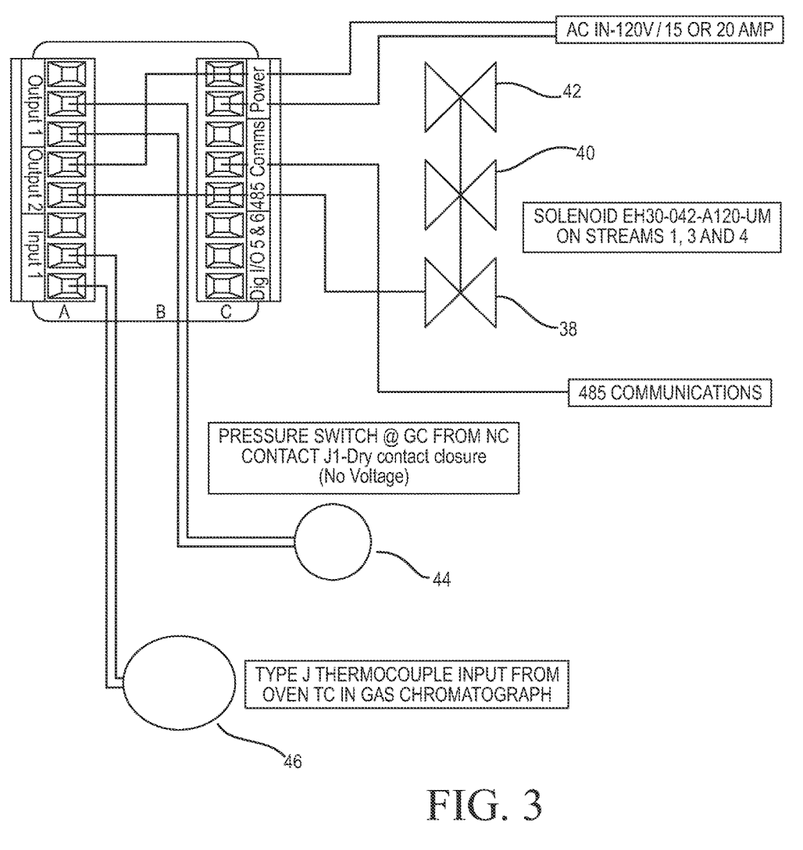
FIG. 3 is a schematic of automatic sample shutoff circuitry associated with the embodiment of FIG. 2.

Turning to a variant of the above-described embodiment, the embodiment of FIG. 2 incorporates a sample conditioner shutdown system to prevent liquid incursion from the system output to an associated chromatograph for protection of the analyzer. In this embodiment, the PID controller 37 is an encased dual controller available again from Watlow as a Watlow Dual Controller (EZ-Zone). The illustrated embodiment features three solenoid controlled shut off valves disposed at select points along the sample pathway which are activated upon detection of an abnormal conditioning system parameter, e.g., heat, pressure, flow rate, back pressure, post-vaporization liquid detection, and even loss of system power. The redundancy of the shutoff valves is employed to maintain the system components at in operational readiness until the deviant parameter is corrected. This shutdown system valves off the flow of liquid if the temperatures monitored falls below a set point in either the sample conditioner cabinet components and even of the analyzer (i.e., the oven of a gas chromatograph) monitored through a thermocouple 46 connected to the controller (See FIG. 3). Pressures are monitored using conventionally disposed pressure transmitters that may be associated for example with the illustrated pressure gauges 16 and 24. Back pressure sensor/transmitters may also be included to compare against supply pressures. A further pressure switch 44 electrically controlled by the dual controller 37 may be incorporated into the system to insure that the analyzer carrier gas is sufficient for GC operation. In the event the carrier gas falls below a threshold pressure, e.g., 75 psig, the normally closed contact opens and idles the chromatograph and sample input thereto until the issue is corrected. Although not illustrated, the system can readily incorporate one or more electronic flow meters disposed along the sample pathway to insure that vaporized sample flow rates fall within acceptable parameters.

Upon detection of undesirable conditions or deviations capable of disabling an associated analyzer, i.e., too high a sample pressure, too low a sample temperature, or detection of liquid and resulting analyzer flooding, the shutdown embodiment of this invention electronically links the 30 controller which signals solenoids 38, 40, and 42 that control for example a conventional pneumatically actuated ball valve to shut down fluid sample input to the vaporizer, vaporized sample input to the heated regulator and sample output from the conditioner to the associated analyzer.

Figure 4:
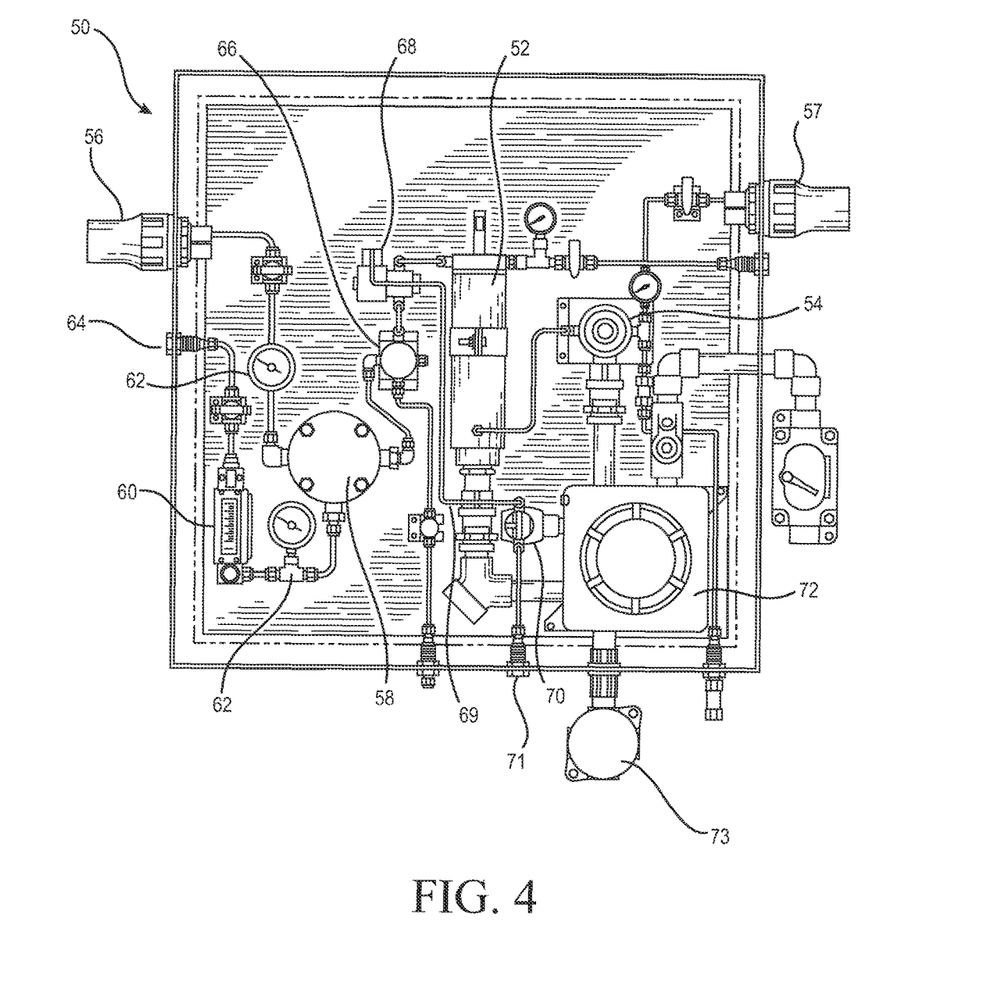
FIG. 4 is a schematic illustration of an embodiment of a shutdown system in accordance with a further aspect of this invention.

Referring now to FIG. 4, it illustrates a shutdown system incorporated into liquid sample conditioning system. The system is contained in a housing 50 which features a standard configuration sample vaporizer 52 and heated pressure regulator 54. In this embodiment, a sample from a select sampling point passes into the cabinet 50 via process sample inlet 56 and ultimately passes to the analyzer via sample output 57. The liquid sample pathway first leads from the input 56 to a filtered liquid speed loop featuring a filter member 58, preferably a self-cleaning 0.5 micron particulate filter such as a 602 T Tornado Filter, a bypass flow indicator 60, pressure gauge references 62disposed both upstream and downstream of the filter member 58, with a return to process 64 and metered inlet and outlet. The filtered sample moves through appropriate tubing from the filter member 58 to a coalescing filter 66 for removal of aerosol and large droplets of liquids in sample stream (via a drain) which is particularly important when an oil may be present. The incorporation of filtering elements is optional unless particular circumstances so require, i.e., high oil content, large aerosol droplets, etc.

From the coalescing filter, the sample path lead to the vaporizer 52 which itself, as disclosed above, can feature a liquid speed loop featuring a built-in bypass. However, before the sample path reaches the vaporizer a solenoid actuated liquid interrupt valve 68 is interposed in the line. The interrupt valve 68 preferably is air actuated valve and blocks liquid flow into the vaporizer from the filters. The air is provided from an external source (e.g., nitrogen cylinder) through airline 69 from an instrument airport 71. The valve 68 is actuated by instrument air supplied by through pneumatic line 69 from a solenoid valve 70 electrically connected to the PID Controller 72. The solenoid valve 70 is normally closed when de-energized that is, it shuts off flow automatically in the event of a power loss. The PID controller can also de-energize the Solenoid in the event a monitored system parameter deviates beyond a select threshold, e.g., the controller signal the Solenoid to opens its contacts if the temperature drops below the application specific set point. In the case of multiple analyzer arrays disposed along a processing pathway, by continuously monitoring the temperatures, the sample conditioner 50, utilizing an integrated communication facility 73, i.e., a RS485 communication port, can send discrete alarm signals to downstream analyzers or digital control systems.

Accordingly, liquids or phase-separated vapor samples are blocked from entering the analyzer, which serves to prevent both distorted sample component analysis and/or analyzer damage. The shutoff embodiment also contemplates conditioner system sample flow shutdown in the event of a power failure. Power failures inevitably create pressure issues and significant temperature losses for samples just exiting the heated regulator. In the event of a power failure complete vaporization is impacted and phase separation readily occur for samples exiting the vaporizer flash chamber. Consequently, the present invention provides analyzer and data protection that has not been available in this application.

Although most applicable to NGL sample processing, the shutoff system contemplated herein is also applicable to monitor conditioning parameters in a variety of vaporized sample streams processed for introduction to analyzers.

The illustrated embodiments of the invention have been provided in the forgoing specification. It should be understood by those skilled in the art that many modifications and embodiments of the invention will come to mind to which the invention pertains, having benefit of the teaching presented in the foregoing description and associated drawing. Therefore, it also should understood that the invention is not limited to the specific embodiments disclosed herein, and that many modifications and other embodiments of the invention are intended to be included within the scope of the invention. Moreover, although specific terms are employed herein, they are used only in generic and descriptive sense, and not for the purposes of limiting the description invention.

INDUSTRIAL APPLICABILITY

The invention combines an system for properly collecting, conditioning and communicating uniform vaporized samples from a non-cryogenic liquid source such widegrade containing Natural Gas Liquid (NGL) from liquid input to an associated analyzer minimizing phase separation and reliquification that skew qualitative and quantitative constituent analysis and/or flood and damage the analyzer. In one embodiment, the invention also incorporates a shutdown system to isolate sample introduction to the analyzer while allowing for operational conditions to be maintained in the conditioner system.

We claim:

1. A system for extracting and conditioning for analysis by a gas sample analyzer of a non-cryogenic natural gas liquid sample, the system comprising:
   a) an insulated cabinet,
   b) a non-cryogenic liquid sample input line;
   c) a vaporizer mounted in said insulated cabinet and having a heater configured to flash vaporize the non-cryogenic liquid sample received via the input line;
   d) a heated pressure regulator mounted in said insulated cabinet;
   e) a vaporized sample output line directly connecting an output of the vaporizer to an input of the heated pressure regulator, the heated pressure regulator being configured to adjust a pressure of the vaporized non-cryogenic liquid sample output from the vaporizer;
   f) an output sample gas conduit line to communicate the vaporized non-cryogenic liquid sample to a gas sample analyzer located outside the insulated cabinet, said output conduit line connected at one end to the heated pressure regulator;
   g) a valve configured to interrupt flow of input between the liquid sample input line and the output sample gas conduit line upon conditions deviating from an acceptable operational range; and
   h) a controller electrically connected to the vaporizer and the heated pressure regulator, said controller being connected to an electrical power source, the controller being configured to monitor the temperature and pressure of the vaporized sample outputted from the heated pressure regulator to fall within the acceptable operational range of the gas sample analyzer,
   wherein the controller is configured to control the vaporizer and the heated pressure regulator to maintain the non-cryogenic vaporized liquid sample output from the heated pressure regulator within the acceptable operation range of the gas sample analyzer.

2. The system of claim 1, further comprising a speed loop connected to the vaporizer.

3. The system according to claim 2, further comprising a vent line connected to the heated pressure regulator for pressure relief in the event that the gas sample outputted from the heated regulator is above the acceptable operational range of the gas sample analyzer.

4. The system according to claim 3, further comprising a communication port associated with the controller.

5. The system according to claim 4, further comprising a liquid filter disposed in the sample input line.

6. The system according to claim 5, where the valve is a solenoid actuated valve disposed between the liquid filter and the input of the vaporizer for interrupting flow of the liquid sample to the vaporizer.

7. The system according to claim 1, further comprising a liquid filter disposed in the sample input line and where the valve is a solenoid actuated valve disposed between the liquid filter and the input of the vaporizer for interrupting flow of the liquid sample to the vaporizer.

8. The system according to claim 1, wherein the valve is disposed between the heated pressure regulator and the output sample gas conduit line.

9. The system according to claim 1, further comprising: controlling, via the controller, the valve to interrupt the flow of the non-cryogenic vaporized liquid sample based on the monitoring.

10. A system for extracting and conditioning a non-cryogenic natural gas liquid sample for analysis by a downstream analyzer, the system comprising:
   a) an insulated cabinet;
   b) a non-cryogenic liquid sample input line;
   c) a vaporizer mounted in said insulated cabinet and having a heater configured to flash vaporize the non-cryogenic liquid received from via the input line to a flash-vaporized sample;
   d) a heated pressure regulator mounted in said insulated cabinet;
   e) a vaporized gas sample output line directly connecting an output of the vaporizer to an input of the heated pressure regulator, the heated pressure regulator being configured to adjust a pressure of the vaporized non-cryogenic liquid sample output from the vaporizer;
   f) an output gas conduit line to a gas sample analyzer located outside the insulated cabinet, said output gas conduit line connected at one end to the heated pressure regulator; and
   g) a controller configured to monitor processing conditions in the insulated cabinet by being in operation signal communication with the vaporizer, the heated pressure regulator, a valve configured to interrupt liquid flow into the vaporizer upon detection of processing conditions deviating from pre-set ranges, and pressure transmitters configured to monitor sample pressure as the sample passes through the system to the vaporized sample output line to be within acceptable operation ranges, the controller being connected to an electrical power source,
   wherein the controller is configured to control the vaporizer and the heated pressure regulator to maintain the non-cryogenic vaporized liquid sample output from the heated pressure regulator within the acceptable operation range of the gas sample analyzer; and
   h) a communications port configured to remotely communicate monitored conditions.

11. The system according to claim 10, further comprising a filter and speed loop disposed in the sample input line.

12. The system according to claim 11, where the valve is a solenoid valve electrically connected to the controller and having a normally closed position which upon activation shuts off the sample flow in the non-cryogenic liquid sample input line.

13. The system according to claim 11, further comprising a plurality of solenoid valves electrically connected to the controller, each solenoid valve having a normally closed position which upon activation of a first solenoid valve shuts off liquid flow to the vaporizer and upon activation of a second solenoid valve shuts off vapor sample flow to the gas sample analyzer.

14. The system according to claim 13, further comprising a thermocouple, said thermocouple providing a signal to the controller to actuate the solenoid valves to shut off sample flow when the detected temperature of the gas sample analyzer falls below a pre-determined minimum.

15. The system according to claim 14, further comprising a pressure switch in communication with the controller to idle the gas sample analyzer in the event the carrier gas level falls below a threshold pressure.

16. The system according to claim 15, further comprising a vent line connected to the heated pressure regulator for pressure relief in the event of the gas sample outputted from the heated regulator being above the acceptable operational range of the gas sample analyzer.

17. A system for extracting and conditioning for analysis of a non-cryogenic natural gas liquid sample, the system comprising:
   a) an insulated cabinet;
   b) a liquid sample input line;
   c) a vaporizer mounted inside said insulation cabinet and having a heater for flash vaporizing the non-cryogenic liquid to a vaporized gas sample, said vaporizer being connected to the input line;
   d) a heated pressure regulator mounted inside said insulation cabinet;
   e) a vaporized sample output line, wherein said vaporized sample output line directly connects said vaporizer and said heated pressure regulator, the heated pressure regulator being configured to adjust a pressure of the vaporized gas sample output from the vaporizer;
   f) an output vaporized sample gas conduit line to a vaporized sample analyzer spaced apart and separate from the insulated cabinet, said output conduit line connected at one end to the heated pressure regulator; and
   g) a controller electrically connected to the vaporizer and the heated pressure regulator, said controller being connected to a power source, the controller configured to monitor monitoring the temperature and pressure of the vaporized sample outputted from the heated pressure regulator to fall within an acceptable operation range of the vaporized sample analyzer,
   wherein the controller is configured to control the vaporizer and the heated pressure regulator to maintain the non-cryogenic vaporized liquid sample output from the heated pressure regulator within the acceptable operation range of the vaporized sample analyzer; and
   h) a valve for interrupting flow of input between the liquid sample input line and the output vaporized sample gas conduit line when conditions deviate from the acceptable operational range.

18. The system according to claim 17, further comprising a vent line connected to the heated pressure regulator for pressure relief in the event of the vaporized sample outputted from the heated pressure regulator being above the acceptable operational range of the vaporized sample analyzer.

19. The system according to claim 18, further comprising a communication port associated with the controller.

20. The system according to claim 19, further comprising a liquid filter disposed in the liquid sample input line.

21. The system according to claim 20, further comprising a solenoid actuated valve disposed between the liquid filter and the input of the vaporizer for interrupting flow of the liquid-sample to the vaporizer.

22. A method for extracting and conditioning for analysis by a gas sample analyzer of a non-cryogenic natural gas liquid sample, the method comprising:
   receiving the non-cryogenic liquid sample via an input line;
   flash vaporizing, via a vaporizer mounted in an insulated cabinet, the non-cryogenic liquid sample;
   outputting, from the vaporizer to a pressure heated regulator via a vaporized sample output line directly connecting an output of the vaporizer to an input of the heated pressure regulator, the vaporized non-cryogenic liquid;

adjusting, at the heated pressure regulator, a pressure of the vaporized non-cryogenic liquid sample output from the vaporizer;

outputting, via an output sample gas conduit line, the non-cryogenic vaporized liquid sample to a gas sample analyzer;

a valve configured to interrupt flow of input between the liquid sample input line and the output sample gas conduit line when conditions deviate from an acceptable operational range; and monitoring, via a controller electrically connected to the vaporizer and the heated pressure regulator, the temperature and pressure of the non-cryogenic vaporized liquid sample output from the heated pressure regulator to fall within an acceptable operation range of the gas sample analyzer, controlling, via the controller, the vaporizer and the heated pressure regulator to maintain the non-cryogenic vaporized liquid sample output from the heated pressure regulator within the acceptable operation range of the gas sample analyzer; and controlling, by the controller and based on the monitoring, a valve configured to interrupt flow of input between the liquid sample input line and the output sample gas conduit line upon conditions deviating from the acceptable operational range.

\* \* \* \* \*